(12) United States Patent
Nettesheim

(10) Patent No.: US 9,234,832 B2
(45) Date of Patent: Jan. 12, 2016

(54) METHOD AND APPARATUS FOR THE WEATHERABILITY TESTING OF A MATERIAL

(71) Applicant: Reinhausen Plasma GmbH, Regensburg (DE)

(72) Inventor: Stefan Nettesheim, Berlin (DE)

(73) Assignee: Maschinenfabrik Reinhausen GmbH, Regensburg (DE)

(*) Notice: Subject to any disclaimer, the term of this patent is extended or adjusted under 35 U.S.C. 154(b) by 185 days.

(21) Appl. No.: 13/899,255

(22) Filed: May 21, 2013

(65) Prior Publication Data
US 2013/0316459 A1 Nov. 28, 2013

(30) Foreign Application Priority Data

May 22, 2012 (DE) .......................... 10 2012 103 777

(51) Int. Cl.
*G01N 17/00* (2006.01)
(52) U.S. Cl.
CPC .............. *G01N 17/00* (2013.01); *G01N 17/002* (2013.01)
(58) Field of Classification Search
CPC ............................ G01N 17/00; G01N 17/002
USPC .................... 422/53, 68.1; 436/2, 6
See application file for complete search history.

(56) References Cited

U.S. PATENT DOCUMENTS

| | | | | |
|---|---|---|---|---|
| 1,827,530 A * | 10/1931 | Le Grand | ......................... | 600/21 |
| 2,523,322 A * | 9/1950 | Ornstein et al. | ................. | 374/57 |
| 3,029,635 A * | 4/1962 | Fetz | ................................ | 73/147 |
| 3,121,329 A * | 2/1964 | Bennett | ..................... | B64G 7/00 73/147 |
| 3,142,171 A * | 7/1964 | Royen | ..................... | G01N 17/00 34/214 |
| 3,224,266 A * | 12/1965 | Klippert | ...................... | 73/150 R |
| 3,309,300 A * | 3/1967 | Grosse et al. | .................. | 204/176 |
| 3,327,536 A * | 6/1967 | Fitzgerald | .................... | 73/865.6 |
| 3,488,681 A * | 1/1970 | Mita et al. | ........................ | 374/57 |
| 3,664,188 A * | 5/1972 | Kockott | ............... | G01N 17/004 250/453.11 |
| 3,675,477 A * | 7/1972 | Allen | .................... | G01N 17/004 250/429 |

(Continued)

FOREIGN PATENT DOCUMENTS

| | | |
|---|---|---|
| CN | 101093228 A | 12/2007 |
| CN | 101226128 A | 7/2008 |

(Continued)

OTHER PUBLICATIONS

Wang, C. X. et al, Surface & Coatings Technology 2007, 201, 6273-6277.*

(Continued)

*Primary Examiner* — Arlen Soderquist
(74) *Attorney, Agent, or Firm* — Simpson & Simpson, PLLC

(57) ABSTRACT

A method and an apparatus (1) for weatherability testing of a material sample (3) are disclosed. The material sample (3) is exposed to a testing atmosphere (12) in a testing chamber (2). The testing atmosphere (12) is formed by a plasma (10). Testing atmosphere (12) is withdrawn from the testing chamber (2) and resupplied to the plasma generation as a process gas (5G), after filtering and/or conditioning. At least one further substance (8S) may be added to a process gas (5G) for plasma generation, in order to obtain a desired chemical composition of the testing atmosphere (12). Parameters of the testing atmosphere (12) like temperature and chemical composition may be controlled. The material sample (3) may furthermore be exposed to UV light (25), which preferably is generated by an electric arc.

28 Claims, 3 Drawing Sheets

(56) References Cited

U.S. PATENT DOCUMENTS

| | | | | |
|---|---|---|---|---|
| 3,709,026 | A * | 1/1973 | Rhodes et al. | 73/12.11 |
| 3,886,791 | A * | 6/1975 | Grossman | G01N 17/00 73/150 R |
| 3,983,742 | A * | 10/1976 | Suga | 374/57 |
| 4,012,954 | A * | 3/1977 | Klippert | 73/150 R |
| 4,111,753 | A * | 9/1978 | Folsom | B01L 1/00 312/1 |
| 4,184,096 | A * | 1/1980 | Suga | H01J 61/52 313/17 |
| 4,627,287 | A * | 12/1986 | Suga | 73/865.6 |
| H0000229 | H * | 3/1987 | Phillips | 165/96 |
| 4,704,903 | A * | 11/1987 | Suga et al. | 73/159 |
| 4,760,748 | A * | 8/1988 | Katayanagi et al. | 73/865.6 |
| 4,770,031 | A * | 9/1988 | Roth et al. | 73/147 |
| 4,807,247 | A * | 2/1989 | Robbins, III | 374/57 |
| 4,817,447 | A * | 4/1989 | Kashima et al. | 73/865.6 |
| 4,931,655 | A * | 6/1990 | Yoshida | G01N 17/00 250/492.1 |
| 4,957,011 | A * | 9/1990 | Huber et al. | 73/865.6 |
| 4,983,526 | A * | 1/1991 | Suga | G01N 17/00 436/135 |
| 4,995,273 | A * | 2/1991 | Kisima et al. | 73/865.6 |
| 5,044,211 | A * | 9/1991 | Whitaker | 73/866 |
| 5,136,886 | A * | 8/1992 | Neigoff et al. | 73/865.6 |
| 5,226,318 | A | 7/1993 | Huber et al. | |
| 5,281,535 | A | 1/1994 | Wei et al. | |
| 5,381,701 | A * | 1/1995 | Frankenthal et al. | 73/865.6 |
| 5,476,636 | A * | 12/1995 | Tomiita et al. | 422/53 |
| 5,503,032 | A * | 4/1996 | Tikhtman et al. | 73/865.6 |
| 5,578,280 | A * | 11/1996 | Kazi et al. | 422/186.07 |
| 5,610,344 | A * | 3/1997 | Ueda et al. | 73/865.6 |
| 5,767,423 | A * | 6/1998 | Camp et al. | 73/865.6 |
| 5,854,433 | A * | 12/1998 | Patel | G01N 17/004 73/159 |
| 6,022,456 | A * | 2/2000 | Manning | 204/176 |
| 6,533,452 | B1 * | 3/2003 | Hardcastle, III | 374/57 |
| 6,591,701 | B2 * | 7/2003 | Suga | 73/865.6 |
| 6,604,436 | B1 * | 8/2003 | Lewandowski et al. | 73/865.6 |
| 6,626,052 | B1 * | 9/2003 | Martin et al. | 73/865.6 |
| 6,659,638 | B1 * | 12/2003 | Hardcastel, III | 374/57 |
| 6,820,509 | B2 * | 11/2004 | Lewandowski et al. | 73/865.6 |
| 6,990,868 | B2 * | 1/2006 | Hardcastle, III | 73/865.6 |
| 7,141,755 | B2 | 11/2006 | Akahori et al. | |
| 7,222,548 | B2 * | 5/2007 | Wass et al. | 73/865.6 |
| 7,572,998 | B2 * | 8/2009 | Mohamed et al. | 219/121.5 |
| 7,784,367 | B2 * | 8/2010 | Kojima et al. | 73/865.6 |
| 7,908,936 | B2 | 3/2011 | Mayer | |
| 8,425,852 | B2 * | 4/2013 | Matsuuchi et al. | 422/186 |
| 8,471,171 | B2 * | 6/2013 | Price et al. | 219/121.5 |
| 2002/0139005 | A1 * | 10/2002 | Thomas | 34/72 |
| 2003/0033896 | A1 * | 2/2003 | Borowczak et al. | 73/866 |
| 2004/0093965 | A1 * | 5/2004 | Hardcastle, III | 73/865.6 |
| 2004/0123682 | A1 * | 7/2004 | Grossman et al. | 73/865.6 |
| 2004/0141036 | A1 * | 7/2004 | Ishikawa | 347/97 |
| 2005/0115931 | A1 | 6/2005 | Akahori et al. | |
| 2006/0028145 | A1 * | 2/2006 | Mohamed et al. | 315/111.21 |
| 2007/0051906 | A1 * | 3/2007 | Brennan | G01N 17/002 250/504 R |
| 2007/0258855 | A1 * | 11/2007 | Turcot et al. | 422/33 |
| 2008/0156070 | A1 * | 7/2008 | Kojima et al. | 73/23.2 |
| 2008/0260578 | A1 * | 10/2008 | Engemann et al. | 422/56 |
| 2009/0121638 | A1 * | 5/2009 | Price et al. | 315/111.21 |
| 2010/0083520 | A1 * | 4/2010 | Bertakis | 34/60 |
| 2010/0209293 | A1 * | 8/2010 | Ikawa et al. | 422/22 |
| 2010/0296977 | A1 * | 11/2010 | Hancock | 422/186 |
| 2011/0168674 | A1 | 7/2011 | Mayumi et al. | |
| 2011/0286908 | A1 * | 11/2011 | Matsuuchi et al. | 423/400 |
| 2012/0145930 | A1 * | 6/2012 | Kuwabara et al. | 250/504 R |
| 2012/0279519 | A1 * | 11/2012 | Swanson et al. | 134/1.1 |

FOREIGN PATENT DOCUMENTS

| | | | |
|---|---|---|---|
| CN | 101236165 A | | 8/2008 |
| CN | 101592586 A | | 12/2009 |
| CN | 102149460 A | | 8/2011 |
| DE | 153922 | | 2/1982 |
| DE | 4115586 | | 11/1992 |
| DE | 4236897 | | 5/1994 |
| JP | 2001059809 A | | 3/2001 |
| JP | 2001-194290 | * | 7/2001 |
| JP | 2001208675 | | 8/2001 |
| JP | 2003-139682 | * | 5/2003 |
| JP | 2004077205 A | | 3/2004 |
| JP | 2008139189 | | 6/2008 |
| JP | 2008-216001 | * | 9/2008 |
| JP | 2008216001 | | 9/2008 |
| JP | 2009058344 A | | 3/2009 |

OTHER PUBLICATIONS

Ren, Y. et al, Surface & Coatings Technology 2008, 202, 2670-2676.*

Helber, B. et al, 17th AIAA International Space Planes and Hypersonic Systems and Technologies Conference 2011, San Francisco, California, paper AIAA 2011-2302, 13 pages.*

Falla, N., Surface Coatings International 1998, 375-380.*

Akahori M., Surface Coatings International Part B: Coatings Transactions2006, 89, 163-168.*

Mohamed, A-A. H., S. Suddala, M.A. Malik, and K.H. Schoenbach. "Ozone Generation in an Atmospheric Pressure Micro-Plasma Jet in Air," IEEE Conference Record—Abstracts. The 31st IEEE International Conference on Baltimore, MD, USA Jun. 28-July1, 2004, Piscataway, NJ, USA, IEEE. Center for Bioelectrics, Old Dominion University, 830 Southampton Ave., Suite 5100, Norfolk, VA 23510, Plasma Science, 2004, pp. 211.

Schunk Group, Weiss Umwelttechnik GmbH, Noxious Gas Climate Tests Temperature and Climate Test Chambers Series WK with Noxious Gas Dosing Device Type BSB, Brochure, available at http://www.wut.com/sixcms/media.php/2335/WUT_Noxious%20gas%20test%20chamber%20%28E%29%5B1%5D.pdf (undated); last accessed May 17, 2013.

Schunk Group, Weiss Umwelttechnik GmbH, Corrosion Testing . . . also with Climate Control, Brochure, available at http://www.wut.com/sixcms/media.php/2335/SC%20KWT%2OKKWT%20%28E%29.pdf; created Apr. 24, 2009; last accessed May 17, 2013.

* cited by examiner

METHOD AND APPARATUS FOR THE WEATHERABILITY TESTING OF A MATERIAL

CROSS-REFERENCE TO RELATED APPLICATIONS

This patent claims priority from German Patent Application No. 10 2012 103 777.9, filed on May 22, 2012, which application is incorporated herein by reference in its entirety.

FIELD OF THE INVENTION

The present invention relates to a method for the weatherability testing of a material, wherein a material sample is exposed to a testing atmosphere.

The invention also relates to an apparatus for the weatherability testing of a material.

BACKGROUND OF THE INVENTION

In many technical areas weatherability tests of materials are of considerable importance with respect to economic and safety concerns. Material samples are exposed to environmental conditions which allow for the study of the aging processes of the materials, usually in an accelerated mode.

For organic substances, for example, in particular, elastomer and polymer materials, the ozone-weatherability test is highly important. By exposure to ozone, these materials embrittle very rapidly. On the exposed surfaces, hairline cracks form, which lead to further destruction. Many test methods exist for characterizing the ozone and ultraviolet (UV) light stability of such materials.

For safety relevant lifespan tests, in particular, in the automotive and the aviation sector, extensive corrosion tests are performed. Salt spray chambers allow reproducible, accelerated corrosion tests (salt spray test) according to relevant national and international standards.

Noxious gas tests with specific setups are a known method for determining the effect of corrosive gases on components. Such components may, for example, be components for facilities of the chemical industry or highly stressed components in turbines or process gas compressors.

Systems for weatherability tests, for example, are offered by the company Weiss Umwelttechnik (http:www.wut.com).

German Patent No. 4115586 (Hehl et al.) describes an air conditioning method for a chemical test chamber. The air within an enclosed space can be conditioned by setting its temperature and its humidity.

German Patent No 4236897 (Trubiroha et al.) describes a weathering apparatus for spraying material samples with highly acidic liquids. In addition, the material samples can be exposed to UV light and various gases.

According to these systems, the gases to which the material samples are exposed must be stored. These gases often are corrosive or poisonous and provide a simulation of the effects of environmental contaminants on a material sample. Storage and handling of such gases are problematic. Some substances occurring in typical industrial exposure situations are unstable and must be generated if needed, for example, ozone, radicals, nitrogen oxides, and peroxides to name a few.

BRIEF SUMMARY OF THE INVENTION

An object of the invention is to provide a method by which a weatherability test of materials can be conducted in a cost-effective and safe manner.

This object is achieved by a method for weatherability testing of at least one material sample, including the following steps:
  a) placing the material sample in a testing chamber;
  b) generating a plasma in a plasma generator and releasing a plasma jet into the testing chamber;
  c) forming a defined testing atmosphere in the testing chamber by means of the plasma jet, for the testing atmosphere to affect the material sample;
  d) withdrawing a testing atmosphere from the testing chamber; and
  e) supplying at least a portion of the testing atmosphere, withdrawn from the testing chamber, after filtering and/or conditioning, to the plasma generator as a process gas.

A further object of the invention is to provide an apparatus, with which a weatherability test of materials can be conducted in a cost-effective and safe manner.

This object is achieved by an apparatus for weatherability testing of at least one material sample having a testing chamber for holding the material sample, a plasma generator with a feed system for at least one process gas for the generation of a plasma and an outlet for a plasma jet into the testing chamber for the formation of a defined testing atmosphere, and a recycling system for withdrawing the testing atmosphere from the testing chamber, conditioning of the withdrawn testing atmosphere, and resupplying of the conditioned testing atmosphere as a process gas to the plasma generator.

For the method of the invention, a material sample is placed into a testing chamber. The material sample may be an item composed of one or more materials, for example, glued, welded or soldered materials, or a simple sample of a material.

A plasma is generated in a plasma generator and released into the testing chamber as a plasma jet. The plasma jet forms a defined testing atmosphere in the testing chamber for the material sample to be exposed to the testing atmosphere.

The testing atmosphere contains substances with respect to which the weatherability of the material sample is to be tested. The effects of the testing atmosphere on the material sample are analyzed. Results are obtained from the analysis of the usually detrimental effect of components of the testing atmosphere on the material sample. In order to obtain reliable results, the at least one material sample preferably is exposed to the testing atmosphere according to a defined protocol. A detrimental effect of the testing atmosphere on the material sample in the case of a composed item may show for at least one material the item is composed of, or only in connections between the components of the item, for example, weld seams, solder or glue connections.

A specific type of weatherability test for which the method of the invention may be used are lifespan tests by accelerated corrosion tests and/or other accelerated aging tests already mentioned above, for which relevant national and/or international standards exist. The method of the invention conducts the lifespan tests according to these standards, and generates the testing atmosphere with a plasma. The testing atmosphere is withdrawn from the testing chamber and at least a part of the withdrawn testing atmosphere is filtered and/or conditioned and subsequently supplied to the generation of the plasma as a process gas.

The plasma is generated from at least one process gas and forms the components of the desired testing atmosphere by conversion of the at least one process gas in the plasma and in the plasma jet. The composition of the testing atmosphere is tested and monitored by a sensor. The conversion can, for example, be caused by plasma-chemical processes or high temperature processes. It should be appreciated that as a process gas, i.e., as source material for the generation of the testing atmosphere, substances can be used which are more easily handled and/or stored.

The at least one process gas is air or air of a defined humidity. Oxygen is a possible process gas. Depending on the desired composition of the testing atmosphere, other process gases may also be considered. Desired components of the testing atmosphere for example, are ozone, nitrogen oxides, peroxides, in particular, hydrogen peroxide, hydrogen chloride, nitric acid, or radicals.

For example, out of oxygen or air, ozone can be produced by means of a non-thermal plasma from a dielectric barrier discharge. In an electric arc, nitrogen oxides can be produced from air by plasma-chemical conversion. Humid air can be converted plasma-chemically to atmosphere containing peroxides.

In order to obtain the desired chemical composition of the testing atmosphere at least one further substance is added to the at least one process gas. The addition of the at least one further substance preferably is done within the plasma generator. In particular, the further substance can be added as an aerosol. In specific embodiments, the aerosol contains at least one salt which may be organic or inorganic. By adding salts to the process gas, in particular, a corrosive and/or acidic testing atmosphere can be generated.

In the testing chamber, a directed stream and/or a swirling may be imparted to the testing atmosphere. In this way, the exposure of the material sample to the testing atmosphere can be influenced.

The plasma can, for example, be generated by a pulsed or continuous dielectric barrier discharge or by a continuous or pulsed electric arc. The discharge or the arc, respectively, is generated in the at least one process gas, and in the plasma generated in this way at least a part of the at least one process gas is converted, for example, plasma-chemically or by high temperature processes. The conversion of the process gas can include the conversion of a substance added to the process gas.

Additionally, the material sample is exposed to ultraviolet (UV) light. The UV light is preferably generated by an arc discharge, or more particularly, by the electric arc also generating the plasma.

The temperature, pressure, humidity, the power of hydrogen (pH) value, the ozone content, or, more generally, the chemical composition of the testing atmosphere is controlled.

The apparatus of the invention for the weatherability test of at least one material sample includes a testing chamber for holding the at least one material sample. The apparatus furthermore exhibits a plasma generator with a feed system for at least one process gas for the generation of the plasma, and with an outlet for a plasma jet into the testing chamber for the formation of a defined testing atmosphere. Furthermore, the apparatus includes a recycling system, which is configured to withdraw testing atmosphere from the testing chamber, to condition the withdrawn testing atmosphere, and to resupply the conditioned testing atmosphere to the plasma generator as process gas. Conditioning the withdrawn testing atmosphere may include filtering and/or catalytical treatment of the testing atmosphere.

The apparatus exhibits a feed system for a further substance to the plasma generator.

The testing chamber contains at least one sensor for at least one of the following parameters of the testing atmosphere: temperature, pressure, humidity, pH value, ozone content, chemical composition of the testing atmosphere. A control unit is provided in the apparatus which is configured to control the at least one parameter. The control unit can, for example, control the supply of process gas and/or a further substance to the plasma generator depending on the measurement values obtained by the at least one sensor. Likewise a voltage source, providing the necessary voltage for the generation of the plasma, can be controlled by the control unit. The control unit may, for example, control the frequency, amplitude, and signal shape of an alternating current (AC) or pulsed direct current (DC) voltage.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
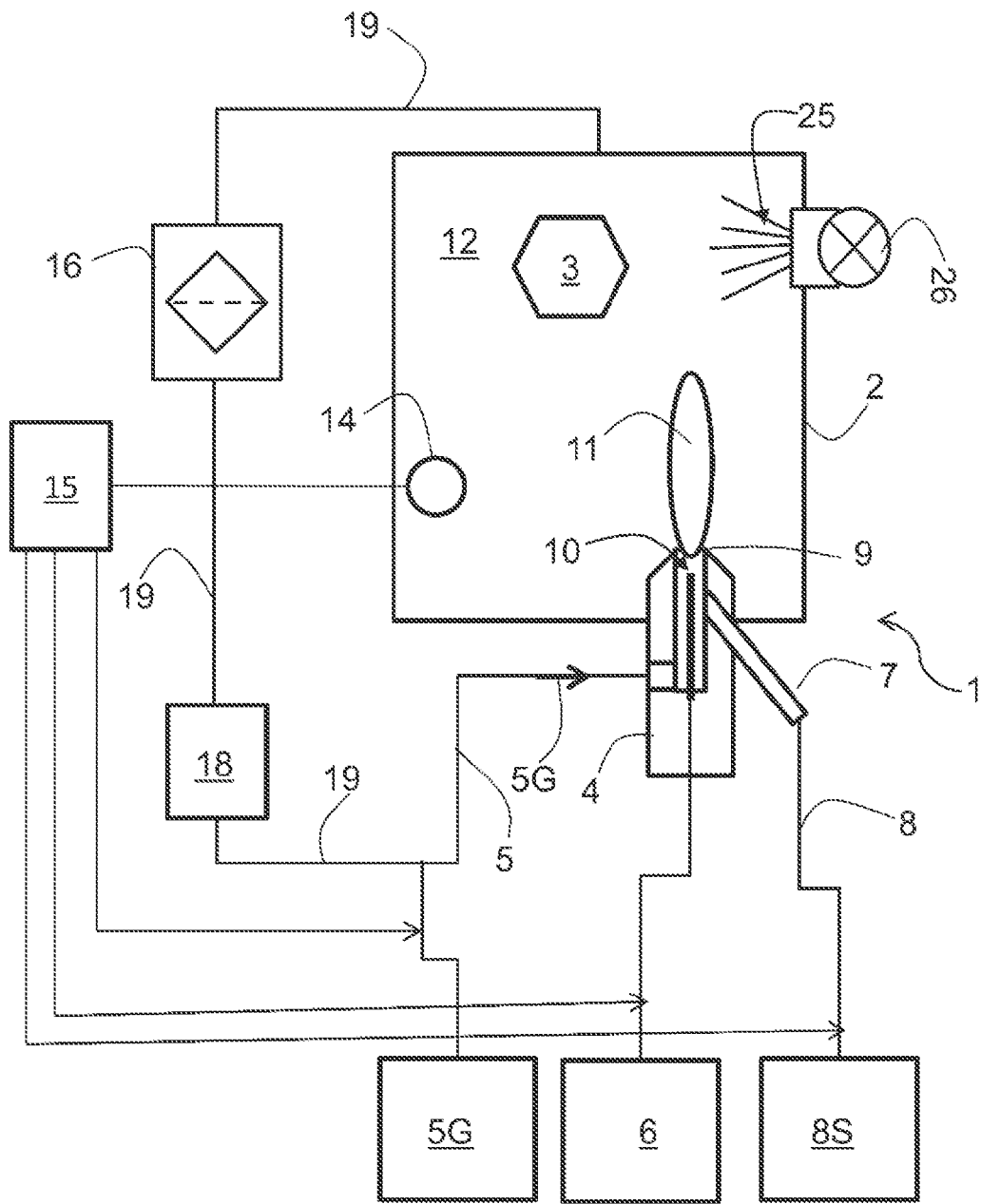
FIG. 1 is a first embodiment of an apparatus of the invention.

FIG. 1 shows a first embodiment of apparatus 1 for the weatherability testing of material sample 3. Material sample 3 is placed in testing chamber 2. Apparatus 1 has plasma generator 4 to which process gas 5G can be supplied from a process gas supply via feed system 5, for example, pipes. Voltage source 6 provides the voltage necessary for the generation of plasma 10 from process gas 5G in plasma generator 4. Plasma generator 4 exhibits injector 7 for at least one further substance 8S, through which further substance 8S can be mixed with process gas 5G in plasma generator 4. Further substance 8S is delivered to injector 7 from a corresponding supply via feed system 8, for example, pipes. Injector 7 may, for example, cause a spraying of delivered further substance 8S, so that delivered further substance 8S is contained in process gas 5G as an aerosol.

Through outlet 9 of plasma generator 4 plasma 10 enters testing chamber 2 through plasma jet 11. Plasma 10 contains converted process gas and thus forms, or maintains, testing atmosphere 12 in testing chamber 2.

Sensor 14 is provided in testing chamber 2. Sensor 14 measures at least one parameter of testing atmosphere 12, for example, temperature or chemical composition, and transmits the measured value of the at least one parameter to control unit 15, by which apparatus 1 is controlled in such a way that the at least one parameter assumes the desired values within a predefined acceptable range of fluctuation. To this end, control unit 15 may control at least feed system 5 for process gas 5G or feed system 8 for further substance 8S or voltage source 6.

Testing atmosphere 12 is withdrawn from testing chamber 2 and supplied to conditioning unit 16. Conditioning unit 16 may include filters and/or catalysts for removing substances from testing atmosphere 12 which would be detrimental to the further process. Pressure generator 18 raises the pressure of the conditioned testing atmosphere to the required value for being supplied to plasma generator 4 via feed system 5 as process gas 5G.

Conditioning unit 16 and pressure generator 18, along with corresponding delivery systems 19, for example, pipes, for the withdrawn or conditioned testing atmosphere are a recycling system for the testing atmosphere.

For operation of apparatus 1, testing chamber 2 may first be filled with an atmosphere, for example, process gas 5G from a supply, from which the desired defined testing atmosphere 12 can be formed by conversion in plasma 10 and plasma jet 11. This atmosphere is passed through plasma generator 4 by the recycling system, wherein at least one further substance 8S may be added. The initial filling of testing chamber 2 may also be done through activated plasma generator 4, and further substance 8S may be added therein. Potential losses of testing atmosphere 12, for example, due to the recycling system, can be compensated from the supply of process gas 5G.

Furthermore, light source 26 for UV light 25 is provided. As part of the weatherability test, material sample 3 and/or testing atmosphere 12 may be exposed to UV light 25. UV light 25 may cause or affect chemical reactions in testing atmosphere 12 and/or material sample 3, which are relevant for the weatherability test, for example, for a lifespan test taking into account the effects of sunlight. In the embodiment shown, separate light source 26 for UV light 25 is used. UV light 25 may, in particular, be generated by an electric arc in light source 26. Where an electric arc is used for the generation of plasma, the electric arc may also be used for the generation of UV light. In this case, a separate UV light source is not necessary, if the UV light generated by the electric arc used for plasma generation meets all requirements for the weatherability test in question. It should be appreciated that in order to use the electric arc generating the plasma as a UV light source the UV light needs to be coupled out from plasma generator 4 and directed, as the case may be, to material sample 3. The UV light can also be filtered.

Figure 2:
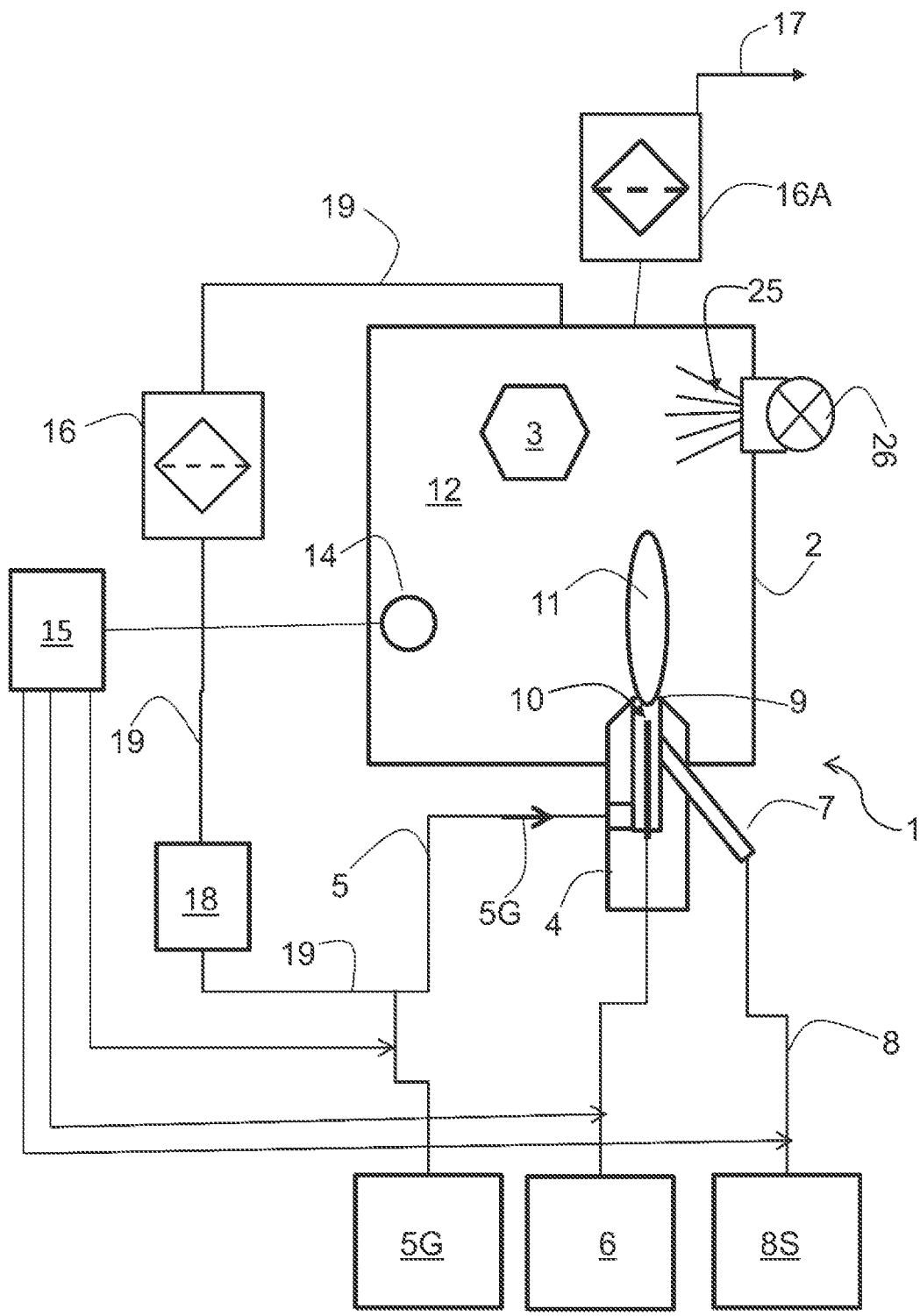
FIG. 2 is a second embodiment of an apparatus of the invention.

FIG. 2 shows a further embodiment of apparatus 1 of the invention. Many of the elements of apparatus 1 shown are already described in the context of FIG. 1.

A part of testing atmosphere 12 withdrawn from testing chamber 2 is delivered to exhaust treatment unit 16A. Exhaust treatment unit 16A may include filters and/or catalysts. The testing atmosphere treated in exhaust treatment unit 16A is discharged to the environment as exhaust 17. The treatment is mainly done to remove chemical compounds created by plasma 10 in process gas 5G from testing atmosphere 12, for example, by filtering and/or catalytical processes. In the weatherability test, the effects of these chemical compounds on material sample 3 are of particular interest. These chemical compounds often are pollutants, so that they need to be removed from testing atmosphere 12 prior to its discharge to the environment. Here, too, it is possible to provide process gas 5G from a supply, be it only at the beginning of the formation of the testing atmosphere, as already mentioned above, or in order to compensate losses due to the partial release of treated testing atmosphere to the environment.

In a modification of the embodiment shown, exhaust 17 may also be released from conditioning unit 16. Depending on the chemical composition of testing atmosphere 12 and the configuration of conditioning unit 16, in this case, separate exhaust treatment unit 16A may be necessary or not.

Figure 3:
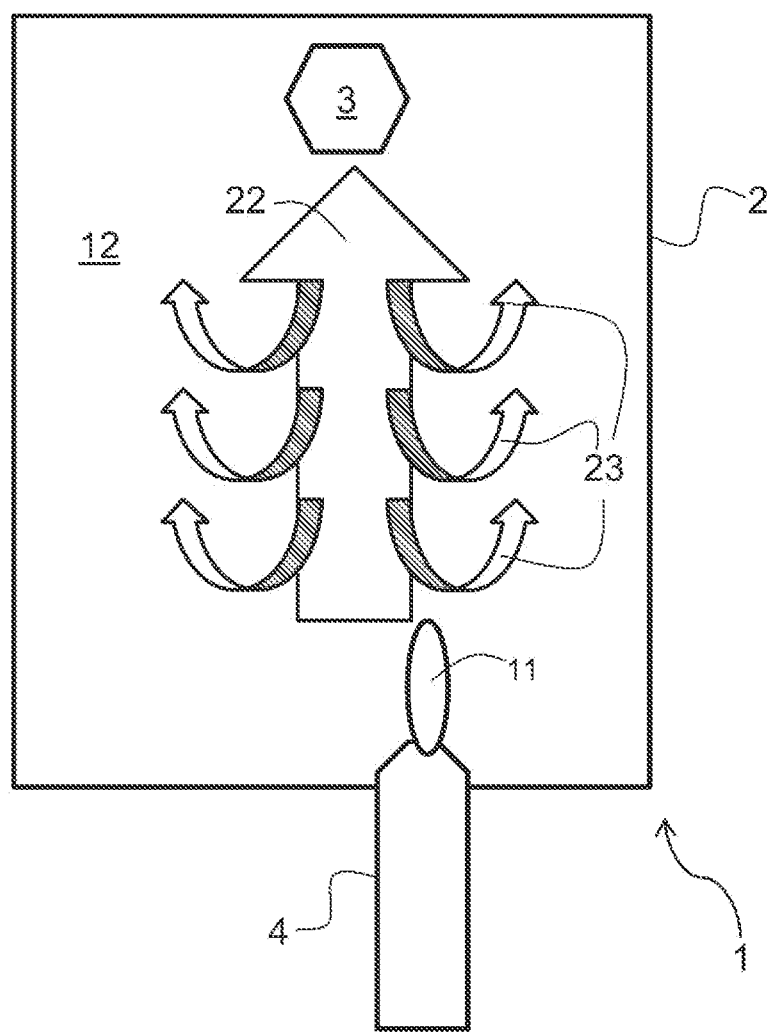
FIG. 3 is a schematic representation of an apparatus of the invention with currents imparted to the testing atmosphere.

FIG. 3 is highly schematic and restricted to a representation of testing chamber 2, plasma generator 4 and material sample 3. In FIG. 3, within testing chamber 2, directed stream 22 and swirling 23 have been imparted to testing atmosphere 12. In this way, the exposure of material sample 3 to testing atmosphere 12 can be influenced. Of course, like in FIG. 3 with swirling 23 and/or directed stream 22 of testing atmosphere 12, elements of apparatus 1 may be present which are already discussed above with respect to FIGS. 1 and 2. Directed stream 22 can, for example, be generated by a fan or imparted to testing atmosphere 12 by the recycling system. Swirling 23 can be created at the entry of the plasma by plasma jet 11 into testing chamber 2 from plasma generator 4. Baffles or obstacles placed in an initially directed stream 22 can be used as well to create swirling 23.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A method for weatherability testing of at least one material sample, comprising the following steps:
   a) placing a material sample in a testing chamber;
   b) generating a plasma in a plasma generator and releasing a plasma jet into said testing chamber, wherein the plasma jet is not directed at the material sample;
   c) forming a defined testing atmosphere in said testing chamber by means of said plasma jet, for said testing atmosphere to affect said material sample;
   d) withdrawing said testing atmosphere from said testing chamber; and,
   e) supplying at least a portion of said testing atmosphere, withdrawn from said testing chamber, after filtering and/or conditioning, to said plasma generator as a process gas.

2. The method recited in claim 1, wherein said testing atmosphere is formed by conversion of at least one process gas in said plasma and in said plasma jet, and wherein a composition of said testing atmosphere is tested and monitored by a sensor.

3. The method recited in claim 2, wherein said at least one process gas is oxygen.

4. The method recited in claim 2, wherein said at least one process gas is air.

5. The method recited in claim 2, wherein said at least one process gas is of a defined humidity.

6. The method recited in claim 2, wherein at least one substance is added to said at least one process gas in said plasma generator in order to obtain a desired chemical composition of said testing atmosphere.

7. The method recited in claim 6, wherein said at least one substance added to said at least one process gas is an aerosol.

8. The method recited in claim 7, wherein said aerosol contains at least one salt.

9. The method recited in claim 1, wherein within said testing chamber a directed stream and/or a swirling is imparted to said testing atmosphere.

10. The method recited in claim 1, wherein a portion of said testing atmosphere withdrawn from said testing chamber is released into an environment.

11. The method recited in claim 1, wherein said plasma is generated by a continuous dielectric barrier discharge.

12. The method recited in claim 1, wherein said plasma is generated by a pulsed dielectric barrier discharge.

13. The method recited in claim 1, wherein said plasma is generated by a continuous electric arc.

14. The method recited in claim 1, wherein said plasma is generated by a pulsed electric arc.

15. The method recited in claim 1, wherein said material sample is exposed to ultraviolet light.

16. The method recited in claim 15, wherein said ultraviolet light is generated by an electric arc.

17. The method recited in claim 1, wherein said testing atmosphere is exposed to ultraviolet light.

18. The method recited in claim 17, wherein said ultraviolet light is generated by an electric arc.

19. The method recited in claim 1, wherein said material sample and said testing atmosphere are exposed to ultraviolet light.

20. The method recited in claim 19, wherein said ultraviolet light is generated by an electric arc.

21. The method recited in claim 1, wherein at least one parameter of said testing atmosphere is controlled and said at least one parameter is selected from the group consisting of temperature, pressure, humidity, pH value, ozone content and chemical composition of said testing atmosphere.

22. An apparatus for the weatherability testing of at least one material sample, comprising:
a testing chamber for holding a material sample,
a plasma generator with a feed system for at least one process gas for the generation of a plasma and an outlet for a plasma jet into said testing chamber for the formation of a defined testing atmosphere, wherein the plasma jet is not directed at the material sample; and,
a recycling system wherein said testing atmosphere is withdrawn from said test chamber, conditioned, and resupplied as a process gas to said plasma generator.

23. The apparatus recited in claim 22, wherein a feed system is provided for feeding a further substance to said plasma generator.

24. The apparatus recited in claim 22, wherein a control unit is provided for controlling at least one parameter of said testing atmosphere and said at least one parameter is selected from a group consisting of temperature, pressure, humidity, pH value, ozone content and chemical composition of said testing atmosphere and wherein said testing chamber contains at least one sensor for said at least one parameter.

25. The apparatus recited in claim 24, wherein said control unit is configured to affect at least said feed system for said at least one process gas.

26. The apparatus recited in claim 24, wherein said control unit is configured to affect a feed system for at least one substance.

27. The apparatus recited in claim 24, wherein said control unit is configured to affect a voltage source for said plasma generator.

28. An apparatus for the weatherability testing of at least one material sample, comprising:
a testing chamber for holding the at least one material sample;
a plasma generator including an outlet at least partially disposed within the testing chamber;
at least one process gas supplied to the plasma generator;
a voltage source arranged to convert the at least one supplied process gas into a plasma to be introduced into the testing chamber via the outlet and form a defined testing atmosphere in the testing chamber, wherein the plasma is not directed at the material sample;;
a first substance suitable to be mixed with the plasma in the plasma generator;
a conditioner arranged to remove a second substance from the defined testing atmosphere; and,
a pressure generator arranged to pressurize the defined testing atmosphere, wherein:
once the testing chamber is filled with the defined testing atmosphere, the defined testing atmosphere flows from the testing chamber to the conditioner, to the pressure generator and to the testing chamber again.

* * * * *